US007887579B2

(12) United States Patent
Mangiardi et al.

(10) Patent No.: US 7,887,579 B2
(45) Date of Patent: Feb. 15, 2011

(54) ACTIVE STENT

(75) Inventors: Eric K. Mangiardi, Charlotte, NC (US);
Tony D. Alexander, Charlotte, NC (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 11/854,234

(22) Filed: Sep. 12, 2007

(65) Prior Publication Data

US 2008/0132998 A1    Jun. 5, 2008

Related U.S. Application Data

(63) Continuation of application No. 10/573,285, filed as application No. PCT/US2004/031898 on Sep. 29, 2004, now abandoned.

(51) Int. Cl.
*A61F 2/06* (2006.01)
(52) U.S. Cl. ................ 623/1.15; 623/1.18; 623/1.2
(58) Field of Classification Search ............... 623/1.15, 623/1.17, 1.18, 1.3, 1.31; 600/191, 194, 600/198; *A61F 2/06*
See application file for complete search history.

(56) References Cited

U.S. PATENT DOCUMENTS

| | | | |
|---|---|---|---|
| 3,818,511 A | 6/1974 | Goldberg et al. |
| 4,441,215 A | 4/1984 | Kaster |
| 4,655,771 A | 4/1987 | Wallsten |
| 4,733,665 A | 3/1988 | Palmaz |
| 4,743,251 A | 5/1988 | Barra |
| 4,800,882 A | 1/1989 | Gianturco |
| 4,820,298 A | 4/1989 | Leveen et al. |
| 4,856,516 A | 8/1989 | Hillstead |
| 4,886,062 A | 12/1989 | Wiktor |
| 5,061,275 A | 10/1991 | Wallsten et al. |
| 5,064,435 A | 11/1991 | Porter |
| 5,102,417 A | 4/1992 | Palmaz |
| 5,104,404 A | 4/1992 | Wolff |
| 5,195,984 A | 3/1993 | Schatz |
| 5,229,431 A | 7/1993 | Pinchuk |
| 5,292,331 A | 3/1994 | Boneau |

(Continued)

FOREIGN PATENT DOCUMENTS

CA     2 212 490 C    10/2006

(Continued)

OTHER PUBLICATIONS

International Search Report for PCT/US2004/031898 completed Jan. 25, 2005.

(Continued)

*Primary Examiner*—Corrine M McDermott
*Assistant Examiner*—Jason-Dennis Stewart
(74) *Attorney, Agent, or Firm*—Stoel Rives LLP

(57) ABSTRACT

The present invention, in an exemplary embodiment, provides a stent, which combines many of the excellent characteristics of both silicone and metal stents while eliminating the undesirable ones. In particular, a principal objective in accordance with the present invention is to provide a family of stents where the relative hardness/softness of regions of the stent can differ from other regions of the stent to provide additional patient comfort and resistance to radial forces. An exemplary embodiment also provides a family of stents with obstruction clearance and/or radiation therapy capabilities.

9 Claims, 2 Drawing Sheets

U.S. PATENT DOCUMENTS

Figure 1:
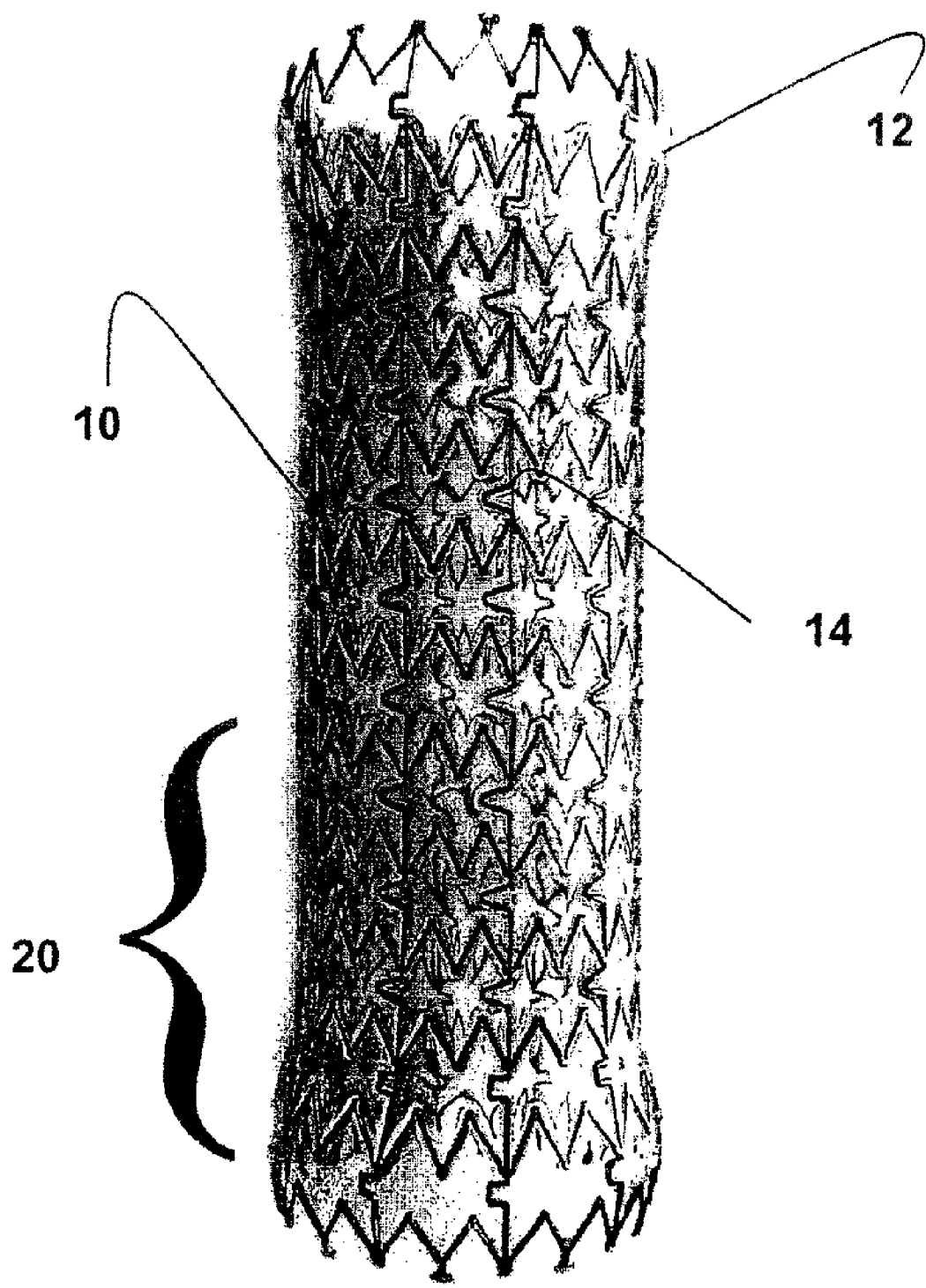

| | | | |
|---|---|---|---|
| 5,383,892 A | 1/1995 | Cardon et al. | |
| 5,383,925 A | 1/1995 | Schmitt | |
| 5,443,498 A | 8/1995 | Fontaine | |
| 5,449,373 A | 9/1995 | Pinchasik et al. | |
| 5,514,154 A | 5/1996 | Lau et al. | |
| 5,534,287 A | 7/1996 | Lukic | |
| 5,540,713 A | 7/1996 | Schnepp-Pesch et al. | |
| 5,562,725 A | 10/1996 | Schmitt et al. | |
| 5,575,818 A | 11/1996 | Pinchuk | |
| 5,591,197 A | 1/1997 | Orth et al. | |
| 5,593,442 A | 1/1997 | Klein | |
| 5,643,312 A | 7/1997 | Fischell et al. | |
| 5,645,559 A | 7/1997 | Hachtman et al. | |
| 5,667,486 A | 9/1997 | Mikulich et al. | |
| 5,674,241 A | 10/1997 | Bley et al. | |
| 5,707,386 A | 1/1998 | Schnepp-Pesch et al. | |
| 5,716,393 A | 2/1998 | Lindenberg et al. | |
| 5,725,572 A | 3/1998 | Lam et al. | |
| 5,733,303 A | 3/1998 | Israel et al. | |
| 5,755,776 A | 5/1998 | Al-Saadon | |
| 5,755,781 A | 5/1998 | Jayaraman | |
| 5,759,192 A | 6/1998 | Saunders | |
| 5,780,807 A | 7/1998 | Saunders | |
| 5,807,404 A | 9/1998 | Richter | |
| 5,814,063 A | 9/1998 | Freitag | |
| 5,827,321 A | 10/1998 | Roubin et al. | |
| 5,836,966 A | 11/1998 | St. Germain | |
| 5,843,120 A | 12/1998 | Israel et al. | |
| 5,860,999 A | 1/1999 | Schnepp-Pesch et al. | |
| 5,876,448 A | 3/1999 | Thompson et al. | |
| 5,876,449 A | 3/1999 | Starck et al. | |
| 5,879,370 A | 3/1999 | Fischell et al. | |
| 5,911,732 A | 6/1999 | Hojeibane | |
| 5,922,019 A | 7/1999 | Hankh et al. | |
| 5,922,020 A | 7/1999 | Klein et al. | |
| 5,935,162 A | 8/1999 | Dang | |
| 5,938,682 A | 8/1999 | Hojeibane et al. | |
| 5,971,950 A | 10/1999 | Lopez et al. | |
| 5,972,018 A | 10/1999 | Israel et al. | |
| 5,980,552 A | 11/1999 | Pinchasik et al. | |
| 6,017,365 A | 1/2000 | Von Oepen | |
| 6,022,371 A | 2/2000 | Killion | |
| 6,027,527 A | 2/2000 | Asano et al. | |
| 6,042,597 A | 3/2000 | Kveen et al. | |
| 6,051,021 A | 4/2000 | Frid | |
| 6,053,873 A * | 4/2000 | Govari et al. | 600/505 |
| 6,053,941 A | 4/2000 | Lindenberg et al. | |
| 6,059,811 A | 5/2000 | Pinchasik et al. | |
| 6,106,548 A | 8/2000 | Roubin et al. | |
| 6,131,266 A | 10/2000 | Saunders | |
| 6,132,461 A | 10/2000 | Thompson | |
| 6,146,403 A | 11/2000 | St. Germain | |
| 6,156,052 A | 12/2000 | Richter et al. | |
| 6,159,142 A | 12/2000 | Alt | |
| 6,171,334 B1 | 1/2001 | Cox | |
| 6,179,867 B1 | 1/2001 | Cox | |
| 6,183,506 B1 | 2/2001 | Penn et al. | |
| 6,193,744 B1 | 2/2001 | Ehr et al. | |
| 6,217,608 B1 | 4/2001 | Penn et al. | |
| 6,231,598 B1 | 5/2001 | Berry et al. | |
| 6,251,134 B1 | 6/2001 | Alt et al. | |
| 6,254,633 B1 * | 7/2001 | Pinchuk et al. | 623/1.3 |
| 6,270,524 B1 | 8/2001 | Kim | |
| 6,273,910 B1 | 8/2001 | Limon | |
| 6,283,992 B1 | 9/2001 | Hankh et al. | |
| 6,293,964 B1 | 9/2001 | Yadav | |
| 6,293,966 B1 | 9/2001 | Frantzen | |
| 6,293,968 B1 | 9/2001 | Taheri | |
| 6,312,459 B1 | 11/2001 | Huang et al. | |
| 6,325,821 B1 | 12/2001 | Gaschino et al. | |
| 6,325,825 B1 | 12/2001 | Kula et al. | |
| 6,336,938 B1 | 1/2002 | Kavteladze et al. | |
| 6,348,065 B1 | 2/2002 | Brown et al. | |
| 6,352,552 B1 | 3/2002 | Levinson et al. | |
| 6,355,063 B1 | 3/2002 | Calcote | |
| 6,375,676 B1 | 4/2002 | Cox | |
| 6,375,677 B1 | 4/2002 | Penn et al. | |
| 6,379,380 B1 * | 4/2002 | Satz | 623/1.15 |
| 6,409,754 B1 | 6/2002 | Smith et al. | |
| 6,413,271 B1 | 7/2002 | Hafeli et al. | |
| 6,416,540 B1 * | 7/2002 | Mathur | 623/1.15 |
| 6,423,084 B1 | 7/2002 | St. Germain | |
| 6,423,091 B1 | 7/2002 | Hojeibane | |
| 6,428,570 B1 | 8/2002 | Globerman | |
| 6,432,133 B1 | 8/2002 | Lau et al. | |
| 6,436,133 B1 | 8/2002 | Furst et al. | |
| 6,440,162 B1 | 8/2002 | Cox et al. | |
| 6,443,982 B1 | 9/2002 | Israel et al. | |
| 6,451,049 B2 | 9/2002 | Vallana et al. | |
| 6,461,380 B1 | 10/2002 | Cox | |
| 6,461,381 B2 | 10/2002 | Israel et al. | |
| 6,464,720 B2 | 10/2002 | Boatman et al. | |
| 6,464,722 B2 | 10/2002 | Israel et al. | |
| 6,471,721 B1 | 10/2002 | Dang | |
| 6,475,236 B1 | 11/2002 | Roubin et al. | |
| 6,478,815 B1 | 11/2002 | Alt | |
| 6,488,703 B1 | 12/2002 | Kveen et al. | |
| 6,508,834 B1 | 1/2003 | Pinchasik et al. | |
| 6,514,285 B1 | 2/2003 | Pinchasik et al. | |
| 6,533,805 B1 | 3/2003 | Jervis | |
| 6,533,810 B2 | 3/2003 | Hankh et al. | |
| 6,537,311 B1 * | 3/2003 | Cox et al. | 623/1.15 |
| 6,551,351 B2 | 4/2003 | Smith et al. | |
| 6,569,194 B1 | 5/2003 | Pelton | |
| 6,589,276 B2 | 7/2003 | Pinchasik et al. | |
| 6,602,285 B1 | 8/2003 | Von Oepen et al. | |
| 6,613,079 B1 | 9/2003 | Wolinsky et al. | |
| 6,613,080 B1 | 9/2003 | Lootz | |
| 6,613,081 B2 | 9/2003 | Kim et al. | |
| 6,616,688 B2 | 9/2003 | Von Oepen | |
| 6,616,689 B1 | 9/2003 | Ainsworth et al. | |
| 6,616,690 B2 | 9/2003 | Rolando et al. | |
| 6,620,192 B1 | 9/2003 | Jalisi | |
| 6,620,193 B1 | 9/2003 | Lau et al. | |
| 6,620,201 B1 | 9/2003 | Nadal et al. | |
| 6,623,520 B2 | 9/2003 | Jalisi | |
| 6,635,084 B2 | 10/2003 | Israel et al. | |
| 6,638,300 B1 | 10/2003 | Frantzen | |
| 6,641,608 B1 | 11/2003 | Pulnev | |
| 6,652,572 B2 | 11/2003 | Kugler et al. | |
| 6,652,573 B2 | 11/2003 | Von Oepen | |
| 6,652,579 B1 | 11/2003 | Cox et al. | |
| 6,656,201 B2 | 12/2003 | Ferrera et al. | |
| 6,656,214 B1 | 12/2003 | Fogarty et al. | |
| 6,656,216 B1 | 12/2003 | Hossainy et al. | |
| 6,656,220 B1 | 12/2003 | Gomez et al. | |
| 6,660,019 B1 | 12/2003 | Richter et al. | |
| 6,664,335 B2 | 12/2003 | Krishnan | |
| 6,669,723 B2 | 12/2003 | Killion et al. | |
| 6,673,106 B2 | 1/2004 | Mitelberg et al. | |
| 6,679,911 B2 | 1/2004 | Burgermeister | |
| 6,682,554 B2 | 1/2004 | Oepen et al. | |
| 6,689,162 B1 | 2/2004 | Thompson | |
| 6,692,521 B2 | 2/2004 | Pinchasik | |
| 6,699,278 B2 | 3/2004 | Fischell et al. | |
| 6,706,061 B1 | 3/2004 | Fischell et al. | |
| 6,709,453 B2 | 3/2004 | Pinchasik et al. | |
| 6,709,454 B1 | 3/2004 | Cox et al. | |
| 6,712,843 B2 | 3/2004 | Elliott | |
| 6,712,844 B2 | 3/2004 | Pacetti | |
| 6,716,240 B2 | 4/2004 | Fischell et al. | |
| 6,719,782 B1 | 4/2004 | Chuter | |
| 6,723,118 B1 | 4/2004 | Ballou et al. | |
| 6,723,119 B2 | 4/2004 | Pinchasik et al. | |

| | | |
|---|---|---|
| 6,723,121 B1 | 4/2004 | Zhong |
| 6,730,116 B1 | 5/2004 | Wolinsky et al. |
| 6,730,117 B1 | 5/2004 | Tseng et al. |
| 6,730,120 B2 | 5/2004 | Berg et al. |
| 6,733,524 B2 | 5/2004 | Tseng et al. |
| 6,736,838 B1 | 5/2004 | Richter |
| 6,736,843 B1 | 5/2004 | Fariabi |
| 6,736,844 B1 | 5/2004 | Glatt et al. |
| 6,740,113 B2 | 5/2004 | Vrba |
| 6,740,114 B2 | 5/2004 | Burgermeister |
| 6,740,115 B2 | 5/2004 | Lombardi et al. |
| 6,743,252 B1 | 6/2004 | Bates et al. |
| 6,746,477 B2 | 6/2004 | Moore |
| 6,746,479 B2 | 6/2004 | Ehr et al. |
| 6,749,629 B1 | 6/2004 | Hong et al. |
| 6,755,856 B2 | 6/2004 | Fierens et al. |
| 6,758,860 B1 | 7/2004 | Penn et al. |
| 6,761,731 B2 | 7/2004 | Majercak |
| 6,764,505 B1 | 7/2004 | Hossainy et al. |
| 6,764,506 B2 | 7/2004 | Roubin et al. |
| 6,764,507 B2 | 7/2004 | Shanley et al. |
| 6,770,088 B1 | 8/2004 | Jang |
| 6,770,089 B1 | 8/2004 | Hong et al. |
| 6,773,445 B2 | 8/2004 | Finlay et al. |
| 6,776,022 B2 | 8/2004 | Kula et al. |
| 6,776,793 B2 | 8/2004 | Brown et al. |
| 6,776,794 B1 | 8/2004 | Hong et al. |
| 6,790,227 B2 | 9/2004 | Burgermeister |
| 6,796,997 B1 | 9/2004 | Penn et al. |
| 6,808,533 B1 | 10/2004 | Goodwin et al. |
| 6,814,749 B2 | 11/2004 | Cox et al. |
| 6,818,013 B2 | 11/2004 | Mitelberg et al. |
| 6,818,014 B2 | 11/2004 | Brown et al. |
| 6,818,015 B2 | 11/2004 | Hankh et al. |
| 6,818,247 B1 | 11/2004 | Chen et al. |
| 6,821,291 B2 | 11/2004 | Bolea et al. |
| 6,821,292 B2 | 11/2004 | Pazienza et al. |
| 6,821,293 B2 | 11/2004 | Pinchasik |
| 6,830,638 B2 | 12/2004 | Boylan et al. |
| 6,833,004 B2 | 12/2004 | Ishii et al. |
| 6,843,802 B1 | 1/2005 | Villalobos et al. |
| 6,849,086 B2 | 2/2005 | Cragg |
| 6,852,124 B2 | 2/2005 | Cox et al. |
| 6,858,037 B2 | 2/2005 | Penn et al. |
| 6,860,898 B2 | 3/2005 | Stack et al. |
| 6,860,900 B2 | 3/2005 | Clerc et al. |
| 6,863,684 B2 | 3/2005 | Kim et al. |
| 6,866,805 B2 | 3/2005 | Hong et al. |
| 6,875,227 B2 | 4/2005 | Yoon |
| 6,878,162 B2 | 4/2005 | Bales et al. |
| 6,881,221 B2 | 4/2005 | Golds |
| 6,881,222 B2 | 4/2005 | White et al. |
| 6,881,223 B2 | 4/2005 | Penn et al. |
| 6,887,264 B2 | 5/2005 | Penn et al. |
| 6,896,696 B2 | 5/2005 | Doran et al. |
| 6,896,697 B1 | 5/2005 | Yip et al. |
| 6,896,698 B2 | 5/2005 | Rolando et al. |
| 6,899,729 B1 | 5/2005 | Cox et al. |
| 6,908,624 B2 | 6/2005 | Hossainy et al. |
| 6,911,041 B1 | 6/2005 | Zschecg |
| 6,916,336 B2 | 7/2005 | Patel et al. |
| 6,920,677 B2 | 7/2005 | Dolan et al. |
| 6,955,723 B2 | 10/2005 | Pacetti et al. |
| 6,979,348 B2 | 12/2005 | Sundar |
| 7,004,966 B2 | 2/2006 | Edwin et al. |
| 2002/0123798 A1* | 9/2002 | Burgermeister ............ 623/1.17 |
| 2005/0070990 A1* | 3/2005 | Stinson ................... 623/1.11 |
| 2006/0069424 A1* | 3/2006 | Acosta et al. ............. 623/1.12 |

FOREIGN PATENT DOCUMENTS

| | | |
|---|---|---|
| EP | 0 540 290 A2 | 5/1993 |
| EP | 0 621 015 A1 | 10/1994 |
| EP | 0 732 089 A2 | 9/1996 |
| EP | 1 077 049 A1 | 2/2001 |
| WO | WO-96/09013 A1 | 3/1996 |
| WO | WO-97/04721 A1 | 2/1997 |
| WO | WO-98/28035 A1 | 7/1998 |
| WO | WO-02/00145 A1 | 1/2002 |
| WO | WO 02/00145 A1 | 1/2002 |
| WO | WO-02/100298 A1 | 12/2002 |
| WO | WO 02/100298 A1 | 12/2002 |

OTHER PUBLICATIONS

U.S. Appl. No. 08/246,320, filed May 19, 1994, Burnmeister et al.

Supplementary Partial European Search Report for EP Application No. 04785238.9, dated Oct. 2, 2008.

Examination Report for Canadian Application No. 2,540,120, dated Sep. 30, 2008.

* cited by examiner

ACTIVE STENT

CROSS-REFERENCE TO RELATED APPLICATIONS

This application is a continuation of U.S. application Ser. No. 10/573,285 filed on Mar. 23, 2006 now abandoned, which was a national stage filing under 35 U.S.C. 371 of PCT/US2004/031898 filed Sep. 29, 2004, which International Application was published by the International Bureau in English on Apr. 14, 2005.

BACKGROUND OF THE INVENTION

1. Field of the Invention

The present invention relates generally to medical devices directed to the prevention of luminal occlusion, and more particularly to stents and methods for making and utilizing these stents in the treatment of both benign and malignant conditions wherein the functionality of the stents is determined by geometrical variability of the scaffolding and concomitant interstices.

2. Description of Related Art

Stents are devices that are inserted into a vessel or passage to keep the lumen open and prevent closure due to a stricture, external compression, or internal obstruction. In particular, stents are commonly used to keep blood vessels open in the coronary arteries and they are frequently inserted into the ureters to maintain drainage from the kidneys, the bile duct for pancreatic cancer or cholangiocarcinoma or the esophagus for strictures or cancer. Vascular as well as not vascular stenting has evolved significantly; unfortunately there remain significant limitations with respect to the technology for producing stents suitable to various portions of a patient's anatomy.

Historically, in order to provide a stent with varying characteristics, the stent had to be manufactured from multiple materials, at least one for each characteristic desired. As a result, many of these stents are woven from two or more metals having differing shape-memories for example. Unfortunately, braided stents are vulnerable to premature obsolescence. Moreover, providing multiple material types in a single stent may lead to inconsistent characteristics along the surface area of the stent. This is particularly undesirable when the stent is to be placed in vascular or nonvascular lumens that have been occluded for one reason or another. The stent needs to be stiffer in some regions while more flexible in others. Moreover, as stents become more readily accepted, additional applications will develop.

Radiation therapy is the careful use of high-energy radiation to treat cancer. Particularly, the radiation destroys the cancer cells' ability to reproduce and the body naturally gets rid of these cells. Radiation therapy is a broad term that also includes the use of potentiating agents such as chemotherapy to enhance the radiation efficacy range. Alternatively, a radiation oncologist may use radiation generated by a machine outside a patient's body (external beam radiation therapy). Radiation also may be given with radioactive sources that are put inside the patient (brachytherapy). Unfortunately, both machine and intravenous radiation therapy treatments depend to some extent on systemic delivery. As a result, collateral tissue exposure to the radiation is inevitable. Larger doses of radiation or potentiating agents are required to ensure adequate delivery of a pharmacological effective dosage reaches the target tissue. This results in side effects such as tissue damage, fatigue, fatigue, skin irritation, temporary or permanent hair loss, temporary change in skin color in the treatment area, loss of appetite, nausea and vomiting, sluggish bowels, cramps and diarrhea, infertility or sterility, vaginal dryness or narrowing, impotence and in some cases death. Radiation therapy also can increase your risk of developing a second cancer. These effects generally result from the high doses required to ensure the radiation gets to the target tissue.

Additional limitations of existing devices involve the constraint of flow dynamics through the internal diameter because of their scaffolding architecture. In particular, depending on whether a stent is covered or formed from braided filaments, flow dynamics can be adversely affected. In certain cases, covered stents can cause or exacerbate mucostassis as a result of the interaction of the polymer side chains and the mucous.

Therefore, there remains an existing need for a therapeutic stent that can have varying characteristics along its surface area while being stamped, not braded, from a single base material. Moreover, there is a need for such a therapeutic stent where the relative hardness, softness, flexibility, stiffness and radial force can be modified as a function of geometric considerations rather than material considerations. In particular, there is a need for a stent that is divided into zones so as to allow the stent to have predetermined characteristics in one zone and could conceivably have drastically different characteristics in an adjacent zone so as to allow for stents that can be tailored to anatomical lumens in general and the particular lumen topography of a specific patient in particular. Moreover, a need remains for a stent that is specifically designed to resist adhesion and facilitate the flow of fluids generally and viscid fluids in particular. There also remains a need for the design of radioactive implantable devices that emit predetermined amounts of radiation at the site of implantation to alleviate radiation side effects associated with systemic delivery of radiation therapy. Particular interest is directed principally on the significant reduction in radiation exposure to collateral tissue. Development of implantable device coatings impregnated with radiation potentiating agents to insure radiation penetration; leveraging knowledge of site specific delivery of implantable devices to develop radiation delivery devices for difficult to access organs such as the liver is needed. Therefore, there is a need for site specific limited dosage delivery of biologicals, which creates additional sites available to radiation therapy.

BRIEF SUMMARY OF THE INVENTION

It is a principal purpose of the present invention to provide a stent, in accordance with an exemplary embodiment of the present invention, which combines many of the excellent characteristics of both silicone and metal stents while eliminating the undesirable ones. In particular, it is an objective of a preferred embodiment in accordance with the present invention to provide a stent that is easily installed, yet in alternative embodiments, removable. Moreover the stent in accordance with this embodiment of the present invention would not cause material infections and may be capable of reducing infection. Therefore, a principal objective of a preferred embodiment in accordance with the present invention is to provide a prosthesis that is suitable for both permanent and temporary use while being easy to insert, reposition and remove.

A principal objective of a preferred embodiment of the present invention is to provide a stent that may be stamped from preferably a single material that is capable of maintaining its axial working length when radially compressed. To this end, the stent does not have a seam that could aggravate luminal tissue. In particular, a stent in accordance with the present invention is formed using a tool that molds the stents outer contour as well as its interstices.

It is yet another objective of an exemplary embodiment of the present invention to provide a stent that can be indicated for the treatment of benign and malignant disease and improve the way clinicians treat malignant obstructions.

Still another objective of the present invention is to provide a stent and method for installing the stent that is economical and suitable for routine purposes. Moreover, the stent will have minimal migration, cause minimal tissue granulation, will not foreshorten after deployment and mucociliary clearance will not be problematic.

Yet another objective of an exemplary embodiment in accordance with the present invention is to provide a prosthesis that will have superior internal to external diameter ratio, superior radial force with dynamic expansion, while being suitable for use in pediatric and adult patients with malignant and benign disease.

A principal objective of an exemplary stent in accordance with the present invention is to provide a family of stents where the relative hardness/softness of regions of the stent can differ from other regions of the stent to provide additional patient comfort and resistance to radial forces.

An additional objective in accordance with an exemplary embodiment is to provide a family of stents with novel interstice configurations that facilitate flexibility, durability and/or proper installation.

Still another objective of a preferred embodiment of the present invention is to provide a self-expanding stent having the above benefits that also defines a plurality of apertures at the termini of the stent for, inter alia, removal of the stent.

An additional objective in accordance with a preferred embodiment of the present invention is to provide a stent that can be manipulated by an external source to provide a pulsing action to encourage clearance. Specifically, the stent is designed to contract radially to dislodge any stagnant material in a manner analogous to that of the human vasculature.

Yet another objective in accordance with the present invention is to provide a medical appliance suitable for site-specific delivery of radiation and/or biological therapy. Preferred biologicals are radiation potentiating agents to enhance tissue penetration at low levels of radiation delivery.

Further objectives, features and advantages of the invention will be apparent from the following detailed description taken in conjunction with the accompanying drawings.

BRIEF DESCRIPTION OF THE SEVERAL VIEWS OF THE DRAWING(S)

Figure 2:
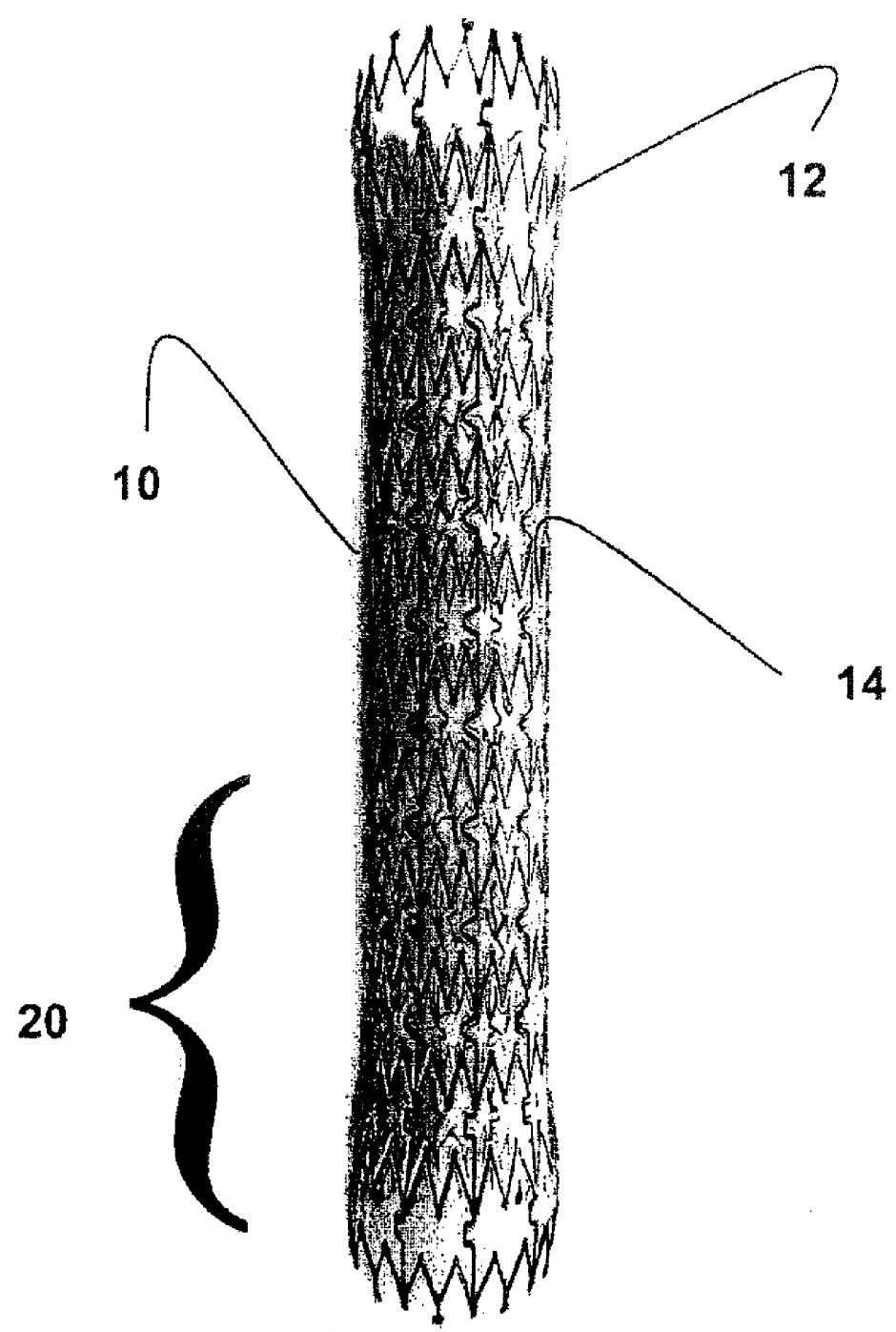

Having thus described the invention in general terms, reference will now be made to the accompanying drawings, which are not necessarily drawn to scale, and wherein:

FIG. 1 is an electron micrograph of an exemplary stent in accordance with the present invention; and FIG. 2 is an electron micrograph of an exemplary stent of FIG. 1 in a compressed configuration.

DETAILED DESCRIPTION OF THE INVENTION

A preferred embodiment of the stent, in accordance with the present invention, provides a stent that prevents epithelialization of the stent and is not subject to premature elongation and foreshortening but is capable of engaging the desired implantation location. The stent also retains its axial length while undergoing radial compression.

The stent is preferably formed from a composite material selected from the group consisting essentially of Ni, C, Co, Cu, Cr, H, Fe, Nb, O, Ti and combinations thereof. The composite material is generally formed into a compressed tube from which the stent is etched and is formed on a suitable shaping device to give the stent the desired external geometry. Both the synthetic collar techniques and in vitro valuation techniques show the remarkable ability of stents in accordance with the present invention to convert acting force into deformation work absorbed by the angled structure, which prevents excessive scaffolding stress and premature material fatigue and accelerated obsolescence.

Preferred embodiments of the present stent comprise small quantities of transition metals such as Scandium, Titanium, Vanadium, Chromium, Manganese, Iron, Cobalt, Nickel, Copper, Zinc, Yttrium, Zirconium, Niobium, Molybdenum, Technetium, Ruthenium, Rhodium, Palladium, Silver, Cadmium, Hafnium, Tantalum, Tungsten, Rhenium, Osmium, Iridium, Platinum, Gold, Mercury, Rutherfordium, Dubnium, Seaborgium, Bohrium, Hassium, Meitnerium, Ununnilium, Unununium, Ununbium. Group 1 transition metals are most amenable to the present application, however, due to the radioactive nature of other transition metals, they may be useful adjuncts for site directed, stent mediated radiation therapy. In such embodiments, the stent itself can be coated with a thin film of the radioactive transition metal, which is relatively stable as a surface coating. When the transition metal is in stent scaffolding itself, the scaffolding contains at least one transition metal of a weight percentage of about between. 01% and 95% and preferably about 5% for demonstrable magnetic activity.

In order to avoid the activation of metalloregulatory proteins or galvanic current, the medical appliances are preferably coated with relatively inert coatings such as a hydrophilic and in certain cases hygroscopic polyurethane or alternatively a transition metal such as tantalum. In preferred embodiments, where biologicals are released from a covered stent, the cover is preferably a biodegradable medical grade polyurethane such as a polylactic polyglycolic acid releasing membrane.

Because of the radioactive nature of some of the transition metals, they must be used in very low quantities. In such cases, to ensure target tissue penetration, the stent and/or the stent covering may be complexed with a radiation potentiator to enhance the signal. Examples of acceptable radiation potentiators or stand alone stent mediated therapies include but are not limited to biologicals such as cis-platinum, paclitaxol, 5-fluorouracial, gemcytobine and navelbine. The chemotherapeutic agents are generally grouped as DNA-interactive Agents, Antimetabolites, Tubulin-Interactive Agents, Hormonal agents and others such as Asparaginase or Hydroxyurea. Each of the groups of chemotherapeutic agents can be further divided by type of activity or compound. The chemotherapeutic agents used in combination with the anti-cancer agents or benzimidazoles of this invention include members of all of these groups. For a detailed discussion of the chemotherapeutic agents and their method of administration, see Dorr, et al, *Cancer Chemotherapy Handbook*, 2d edition, pages 15-34, Appleton & Lange (*Connecticut*, 1994) herein incorporated by this reference.

DNA-Interactive Agents include the alkylating agents, e.g. Cisplatin, Cyclophosphamide, Altretamine; the DNA strand-breakage agents, such as Bleomycin; the intercalating topoisomerase 11 inhibitors, <BR> <BR> e.g., Dactinomycin and Doxorubicin); the nonintercalating topoisomerase 11 inhibitors such as, Etoposide and Teniposide; and the DNA minor groove binder Plcamydin. The alkylating agents form covalent chemical adducts with cellular DNA, RNA, and protein molecules and with smaller amino acids, glutathione and similar chemicals. Generally, these alkylating agents react with a nucleophilic atom in a cellular constituent, such as an amino, carboxyl, phosphate, or sulfhydryl group in nucleic acids, proteins, amino acids, or glutathione. The mechanism and the role of these alkylating agents in cancer therapy are not well understood. Typical alkylating agents include: Nitrogen mustards, such as Chlorambucil, Cyclophosphamide, Isofamide, Mechlorethamine, Melphalan, Uracil mustard; aziridines such as Thiotepa; methanesulfonate esters such as Busulfan; nitroso ureas, such as Cannustine, Lomustine, Streptozocin; platinum complexes, such as Cisplatin, Carboplatin; bioreductive alkylator, such as Mitomycin, and Procarbazine, Dacarbazine and Altretamine; DNA strand breaking agents include Bleomycin; DNA topoisomerase 11 inhibitors include the following: Intercalators, such as Amsacrine, Dactinomycin, Daunorubicin, Doxorubicin, Idarubicin, and Mitoxantrone; nonintercalators, such as Etoposide and Teniposide. The DNA minor groove binder is Plicamycin.

The Antimetabolites interfere with the production of nucleic acids by one or the other of two major mechanisms. Some of the drugs inhibit production of the deoxyribonucleoside triphosphates that are the immediate precursors for DNA synthesis, thus inhibiting DNA replication. Some of the compounds are sufficiently like purines or pyrimidines to be able to substitute for them in the anabolic nucleotide pathways. These analogs can then be substituted into the DNA and RNA instead of their normal counterparts. The Antimetabolites useful herein include: folate antagonists such as Methotrexate and trimetrexate pyrimidine antagonists, such as Fluorouracil, Fluorodeoxyuridine, CB3717, Azacytidine, Cytarabine, and Floxuridine purine antagonists include Mercaptopurine, 6-Thioguanine, Fludarabine, Pentostatin; sugar modified analogs include Cyctrabine, Fludarabine; ribonucleotide reductase inhibitors include Hydroxyurea.

Tubulin Interactive agents act by binding to specific sites on Tubulin, a protein that polymerizes to form cellular microtubules. Microtubules are critical cell structure units. When the interactive agents bind on the protein, the cell cannot form microtubules Tubulin Interactive agents include Vincristine and Vinblastine, both alkaloid and Paclitaxel.

Hormonal agents are also useful in the treatment of cancers and tumors. They are used in hormonally susceptible tumors and are usually derived from natural sources. These include: estrogens, conjugated estrogens and Ethinyl Estradiol and Diethylstilbestrol, Chlorotrianisene and Idenestrol; progestins such as Hydroxyprogesterone caproate, Medroxyprogesterone, and Megestrol; androgens such as testosterone, testosterone propionate; fluoxymesterone, methyltestosterone; Adrenal corticosteroids are derived from natural adrenal cortisol or hydrocortisone. They are used because of their anti-inflammatory benefits as well as the ability of some to inhibit mitotic divisions and to halt DNA synthesis. These compounds include Prednisone, Dexamethasone, Methylprednisolone, and Prednisolone.

Leutinizing hormone releasing hormone agents or gonadotropin-releasing hormone antagonists are used primarily the treatment of prostate cancer. These include leuprolide acetate and goserelin acetate. They prevent the biosynthesis of steroids in the testes.

Antihormonal antigens include antiestrogenic agents such as Tamosifen, antiandrogen agents such as Flutamide; and antiadrenal agents such as Mitotane and Aminoglutethimide. Hydroxyurea appears to act primarily through inhibition of the enzyme ribonucleotide reductase. Asparaginase is an enzyme that converts asparagine to nonfunctional aspartic acid and thus blocks protein synthesis in the tumor.

While the foregoing represents some preferred embodiments of the present invention, other chemotherapeutic agents and coating techniques may be utilized. The principal limitation is that such delivery must alleviate many of the undesirable aspects of the systemic treatment.

Though one skilled in the stent engineering art, once apprised of the present application, would be able to manufacture a stent consistent with the present invention by other methods, a preferred method of manufacturing such stents follows. As stated above a composite material is selected and a blank is formed there from. The blank is preferably laser etched and the etch work is generally verified for accuracy using visual recording microscopy. Dimensional measurements are taken to ensure strut thickness, segment angles, zone placement, etc. Moreover, the stent is preferably formed on a shaping tool that has substantially the desired contour of the external stent dimensions.

In the event the stent is to be shaped to the dimensions of a particular lumen, optical photography and/or optical videography of the target lumen may be conducted prior to stent formation. The geometry of corresponding zones and connector regions of the stent then can be etched and formed in accordance with the requirements of that target lumen. For example, if the stent were designed for the trachea, which has a substantially D shaped lumen and additionally the middle zones needed to be softer than the end zones, the stent could be designed to those specifications. In particular, if the topography of the trachea of a particular patient is captured optically and the appropriate dimension provided, a patient specific prosthesis could be engineered. These techniques can be adapted to other non-vascular lumen but is very well suited for vascular applications where patient specific topography is a function of a variety of factors such as genetics, lifestyle, etc.

It should be pointed out that unlike the use of differing shape memory materials to change regions of a stent, stents in accordance with the present invention can take on an infinite number of characteristic combinations as zones and segments within a zone can be modified by changing angles, segment lengths and segment thicknesses during the etching and forming stages of stent engineering or during post formation processing and polishing steps. Moreover, by modifying the geometry of the connectors between zones, addition functionality may be achieved.

Exemplary stents 10 in accordance with the present invention are shown in FIGS. 1-3 showing the preferred interstice geometry. Not shown is a wide variety of interstice geometries that are also acceptable alternatives to the preferred, namely, U, V, W, Z, S and X geometries to name a few.

The stent 10 also is formed of memory metal and preferably has unique geometrical interstices that are laser etched therein. However, other conventional ways of forming interstices in unitary stents, though not equivalent are contemplated, may be employed and would be within the skill set of one in the art.

It cannot be overemphasized, however, that this does not mean the knowledge that changes in the geometry of interstices affect stent functionality is currently known in the art. To the contrary, the present inventors discovered the interrelation between interstice geometry, width, length and relative resistance to torsional stress and radial force. In fact, it can be said that the stent 10 has circumferential bands extending perpendicularly with respect to the luminal device's longitudinal axis. These bands are referred to generally as zones. A connector 50 connects these bands to one another; the connector 50 is an additional means for adjusting stent functionality. In particular, the connector 50 defines a substantially U shaped member, but could define other geometries such as U, V, W, Z, S and X to name a few.

In a standard orientation, as shown particularly in FIG. 1, the substantially U-shape connector comprises preferably two leg members and a crossing member that connects with and extends perpendicularly at preferably 90° angles with respect to the leg members. It must be noted that alternative angles may be provided without departing materially from the invention. The present inventors discovered that if you modify the length of the crossing member and/or the leg members and/or the angle at which the crossing member and the leg members intersect, the relative hardness/softness, radial force and/or flexibility of the stent 10 could be modified. The angles can be modified at varying acute angles short of 90° or varying obtuse angles greater than 90°. The incremental changes correspondingly change certain characteristics of the stent 10. As a result, different zones of the stent 10 can be given different rigidities to improve patient comfort and for example, in airway stents, to facilitate luminal patency. Moreover, various anatomical lumens may need different degrees of stent rigidity. As a result, stents 10 in accordance with the present invention can be manufactured to exacting specifications to contour properly to various lumens in a patient's anatomy, which may need varying levels of structural support from the medical appliance.

By changing the leg lengths of all the previously discussed legs or individual legs separately, additional stent characteristics can be obtained. The beauty of this system is that the desired characteristics can be determined prior to forming the stent and by staying within certain forming parameters, the stent can be formed, crimped, delivered and deployed with confidence that the desired functionality with result. This is important in light of the fact that both vascular and nonvascular lumen have unique topography. As a result, methods and devices in accordance with the present invention usher in the ability to tailor prosthesis to anatomical tissue in general and particular patient anatomy in particular.

The U shaped connectors have a crossing member and at least two leg members, respectively. The present inventors discovered that if you increase/decrease the length of leg members and/or increase/decrease the length of crossing members and/or vary the angle at which crossing members and leg members intersect, you affect the functionality of the stent. In particular, the shorter the length of the leg members, the less flexibility available in that portion of the stent. By way of example only, if you want to decrease the amount of torsional flexibility of the stent, 10, you would have to modify the connector 40 so that the legs are longer than shown and that the angle formed by legs and crossing member, respectively, is slightly greater than 90°. Alternatively, the length of the crossing member can impact the functionality of the stent as well. The stent can be made more rigid by shortening crossing member or the stent may be made more flexible by lengthening crossing member. It should be noted that the combination of the changes of leg lengths, crossing member lengths, angle variations, shapes and number of connectors provide the stent with the ability to conform to specific lumens in the anatomy of a patient. The result is a form fitting medical prosthesis that may be tailored to specific anatomical lumens in general and to the anatomical lumens of an individual patient in particular.

In a preferred embodiment, the modification of interstice geometries and manipulation of the U shaped connection member to achieve variable stent functionality is provided. The rigidity of the stent scaffolding or interstice matrix along with the torsionality of the stent itself is principally a function of these modifications. In an exemplary embodiment, the stents relative flexibility can be rated soft, medium or hard based on the degree of flex and torsionality. The less torsionality and flex in the stent the harder the stent is rated.

An exemplary stent in accordance with the present invention with relatively great torsionality and radial flexibility would be rated soft. An exemplary soft rated stent comprises distance between U shaped connectors of about 4.5 µm in the compressed state (i.e., contracted in the 3 mm tube subject to laser etching). Moreover, the length of the crossing member is preferably about 1.0 µm. The lengths of the leg members are preferably about 1.5 µm in length. Additionally the leg members may further comprise feet that attached to the remainder of the stent scaffolding. The feet can be adjusted from a standard length of about 0.25 µm to further adjust the characteristics of the stent. There is additionally a substantially rectangular member incorporated in the U shaped connector with similar capacity for variability. The variability factors and results of modifying the dimensions of the substantially rectangular members are similar to those evinced by leg length dimensional modifications.

By way of example, but not to be construed in any way as limiting, the softness index or relative flexibility can be increase by increasing the various lengths discussed above. For example, by increasing the length of the legs and crossing members of the U shaped connector, flexibility increases. However, with respect to the distance between U shaped members and distance between interstices in a preferred stent embodiment, there is an inverse correlation between length and softness. This relative softness/hardness indexing as a corollary of interstice dimensions is a novel aspect of preferred embodiment of the present invention. As a practical rule of thumb, longer leg lengths coupled with acute angles provide for greater flexibility. Conversely, shorter leg lengths and more obtuse angles provide more rigidity. By way of non-limiting example, a U shaped connector with short legs deviating from the crossing member at angles greater than 90°, will be extremely rigid and resistant to torsional strain as compared to a U shaped connector with longer legs diverging from the crossing member at angles less than 90°.

In addition to the length and spacing differences, the interstices themselves may define various shapes that by their very nature afford novel functionality to the stent. The changes of functionality, however, are more a function of the dimensional differences of the various shapes rather than a function of the shapes themselves. Therefore, it is important to keep in mind that the dimensional differences discussed in the previous paragraph are determinative of the functionality accorded the stent by the varying interstice geometries. It is for this reason that one of ordinary skill in the art, after being apprised of the present invention, would be able to conceive of a number of interstice geometries to satisfy certain functionality criteria by keeping certain dimensional parameters constant.

Beyond the geometry determined functionality, enhanced characteristics are provided by the incorporation of magnetic properties such that by changing the polarity of an external object, the stent can be urged to contract upon itself to clear stagnant material in the lumen thereof. In particular the stent contracts radially rather than foreshortening to prevent stent migration. Moreover, because of the substantially dog bone shape of at least one end, when the stent is pulsed and contracts, the dog bone shaped end prevents migration. To this end, the proximal end is preferably the dog bone shaped end in most applications; however, certain lumens require that the radial force retention reside at the distal most end.

A preferred external pulsation source is a magnetic that can be placed about the general area of the implant to cause contraction. Alternatively, a device with reversible magnetic polarity functionality may be provided to achieve the same result. In either case, the stent itself can have varying zones such as 20 in FIG. 1 that has a different magnetic charge than other zones so as to allow the stent to contract in sections along the longitudinal expanse thereof.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes, which come within the meaning and range of equivalency of the claims, are to be embraced within their scope.

That which is claimed:

1. A method of treating a patient with an obstruction inside a medical appliance, comprising the steps of:
    providing a medical appliance comprising a scaffolding, the scaffolding configured to define a substantially cylindrical member having a distal end and a proximal end and extending longitudinally there between, forming a lumen there through, wherein at least a portion of the scaffolding comprises a material that is responsive to a magnetic field;
    radially contracting the cylindrical member in response to exposing the scaffolding to a magnetic field to force an obstruction within the lumen to migrate; and
    activating expansion of the medical appliance to the pre-contracted state.

2. The method of claim 1, wherein radially contracting comprises changing a polarity proximate to the scaffolding.

3. The method of claim 1, wherein radially contracting comprises radially contracting only the proximal or distal end of the cylindrical member.

4. The method of claim 1, wherein providing comprises providing a scaffolding including a plurality of zones of varying magnetic charge such that at least one zone of the cylindrical member is configured to contract in response to exposure to a magnetic field while at least one other zone does not contract in response to exposure to a magnetic field.

5. The method of claim 4, wherein radially contracting comprises radially contracting at least one zone in response to exposure to a magnetic field while at least one other zone does not radially contract in response to exposure to the magnetic field.

6. A method of treating a patient with an obstruction inside a medical appliance, comprising the steps of:
    providing a medical appliance comprising a scaffolding, the scaffolding configured to define a substantially cylindrical member having a distal end and a proximal end and extending longitudinally therebetween, forming a lumen therethrough, wherein at least a portion of the comprises a material that is responsive to a magnetic field, and wherein the cylindrical member comprises a plurality of zones such that at least one zone of the cylindrical member is configured to contract in response to exposure to a magnetic field while at least one other zone does not contract in response to exposure to a magnetic field; and
    radially contracting at least one zone in response to exposing the scaffolding to a magnetic field to force an obstruction within the lumen to migrate while at least one other zone does not radially contract in response to exposure to the magnetic field.

7. The method of claim 6, further comprising activating expansion of the medical appliance to the pre-contracted state.

8. The method of claim 6, wherein radially contracting comprises radially contracting at least one zone corresponding to the proximal or distal end of the cylindrical member.

9. The method of claim 6, wherein providing comprises providing a cylindrical member including a plurality of zones of varying magnetic charge such that at least one zone of the cylindrical member is configured to contract in response to exposure to a magnetic field while at least one other zone does not contract in response to exposure to a magnetic field.

* * * * *